United States Patent
Yale et al.

[11] Patent Number: 5,820,621
[45] Date of Patent: Oct. 13, 1998

[54] MEDICAL FLUID TRANSFER AND DELIVERY DEVICE

[75] Inventors: Mark C. Yale, Westwood, N.J.; Sean P. Daw, Brooklyn, N.Y.

[73] Assignee: Becton, Dickinson and Company, Franklin Lakes, N.J.

[21] Appl. No.: 902,029

[22] Filed: Jul. 29, 1997

[51] Int. Cl.⁶ .................................................. A61B 19/00
[52] U.S. Cl. ........................................ 604/411; 604/263
[58] Field of Search .................................. 604/411, 263, 604/192, 187, 905, 280, 283, 403

[56] References Cited

U.S. PATENT DOCUMENTS

| | | | |
|---|---|---|---|
| 1,558,829 | 10/1925 | Brody . | |
| 2,767,710 | 10/1956 | Blackman | 128/218 |
| 2,845,068 | 7/1958 | Gabriel | 128/221 |
| 3,119,391 | 1/1964 | Harrison | 128/221 |
| 3,234,944 | 2/1966 | Stevens et al. | 128/221 |
| 4,058,121 | 11/1977 | Choksi et al. | 128/221 |
| 4,654,034 | 3/1987 | Masters et al. | 604/192 |
| 4,963,132 | 10/1990 | Gibson | 604/256 |
| 4,969,883 | 11/1990 | Gilbert et al. | 604/414 |
| 5,092,852 | 3/1992 | Poling | 604/192 |
| 5,364,387 | 11/1994 | Sweeney | 604/411 |
| 5,405,331 | 4/1995 | Behnke et al. | 604/167 |
| 5,411,492 | 5/1995 | Sturman et al. | 604/263 |

*Primary Examiner*—John D. Yasko
*Attorney, Agent, or Firm*—Arthur D. Dawson

[57] ABSTRACT

A fluid transfer device for accessing fluid from vials and ampoules includes a cannula assembly that defines an axis. The cannula assembly includes a cannula with a proximal end, a distal end and a lumen therethrough. The cannula assembly also has a hub fixedly attached to the proximal end of the cannula that has an open proximal end in fluid communication with the lumen. The fluid transfer device has a filling straw with a proximal end, a distal end and a passageway therethrough and a housing with an outside surface that is fixedly attached to the proximal end of the straw. The housing has a cavity therein to coaxially receive at least a portion of the cannula assembly to form a fluid path between the open proximal end of the hub and the distal end of the filling straw. The fluid transfer device also has a removable shield with an open proximal end, a distal end, an outside surface, and a sidewall that defines a receptacle therein. The shield is rotatable with respect to the housing from a first position wherein the shield is removable from the housing to expose the filling straw for use and a locked position wherein the shield and the housing are locked together to form a unitary structure removable from hub to expose the cannula. The outside surface of the housing and the outside surface of the shield include an indication of the shield's rotational position with respect to the housing.

17 Claims, 8 Drawing Sheets

MEDICAL FLUID TRANSFER AND DELIVERY DEVICE

FIELD OF INVENTION

The invention is generally related to a device mountable on a hypodermic syringe or other medical fluid handling device. More particularly, the invention allows a practitioner to access an injectable liquid medicament contained in ampoules or vials with elastomeric closures to fill the syringe with the liquid medicament for subsequent delivery to a patient.

BACKGROUND

Liquid injectable medicaments are often stored in sealed ampoules with a frangible seal or vials with elastomeric closures. Practitioners generally access the ampoules by breaking the seal, and withdrawing the liquid through a conventional hypodermic needle into a syringe. When the medicament container is a vial with an elastomeric closure, the practitioner generally uses a conventional sharp hypodermic needle on a syringe to penetrate the closure and withdraws the medicament into the syringe. Conventionally, the filled syringe with the hypodermic needle is then used to administer the medicament directly to the patient, or to penetrate a septum on an intravenous (I.V.) set and deliver the medicament to the patient through a catheter. With the wide recognition of the hazards of blood borne pathogens by the medical community, device manufacturers have developed alternatives to conventional hypodermic needles for transferring medicaments from sealed vials and administering the medicaments to patients. Alternative transfer devices include the needleless I.V. sets that incorporate pre-slit septa that are accessible by a blunt cannula. These blunt cannula/pre-slit systems are widely available from several manufacturers. While the blunt cannula/slit septum system is very useful for transfer of a medicament from an already filled syringe into an I.V. delivery system, the problem of filling the syringe from a sealed ampoule or a vial with an elastomeric closure is not solved by the pre-slit septum/blunt cannula system.

Many commonly used medicaments are supplied lyophilized and are reconstituted under sterile conditions just prior to usage. These lyophilized materials are generally supplied sterile in air-tight containers that either have a frangible seal or a monolithic elastomeric closure to protect the contents from moisture, microbial contamination, and in some cases, oxygen. These same type containers are also commonly used for aqueous solutions of medicaments. Ampoules with frangible seals and vials with monolithic elastomeric closures are not easily accessible by blunt cannula devices. As a result, device manufacturers developed filling devices known as "filling straws" or "filling spikes". These devices are somewhat similar in appearance to hypodermic needles, but have a larger diameter and bulky appearance indicative of their intended usage, i.e., puncturing of septa, not patient's tissue. The filling straws generally have a sharpened beveled point at their distal ends, but the bevel shape is generally designed to penetrate septa without coring, rather than being designed to penetrate tissue. Ampoules are generally made of glass with a weakened area that allows the practitioner to break off the top and provide access to the ampoule's contents. The filling straws are generally mounted on a syringe and have a small enough diameter and sufficient length to be used to reach into an opened ampoule and withdraw the contents. When the filling straws are used on a vial with an elastomeric closure, the beveled point is used to penetrate the closure and provide access to the contents. Since the filling straws are designed to penetrate septa and generally present a too "formidable" appearance to be used for patient's tissue penetration, they generally are used as intended by the manufacturer. A practitioner may use a filling straw to withdraw a medicament into a syringe and then remove the filling straw and attach the syringe directly to an I.V. set by utilizing a P.R.N. adapter. (P.R.N. is an acronym for the Latin term pro re nata, literally translated "as the need arises".) Alternatively, a practitioner may choose to remove the filling straw and attach a blunt cannula to the syringe, then access the I.V. set through a pre-slit septum. These alternatives generally eliminate the need for sharp hypodermic needles, but according to most hospital sharps usage protocols, the sharpened filling spike is still treated as a sharp and requires special handling and disposition.

Device manufacturers strive to simplify the usage of filling and transfer devices for practitioners. Filling straws that incorporate a blunt cannula are available. These devices have a filling straw with a distal void that accepts a blunt cannula with a shield over the filling straw. When a practitioner uses such a combination device by removing the shield, either the filling straw or the blunt cannula may be inadvertently exposed. If a device was available that prevented inadvertent exposure of the sharpened filling straw, the art of filling syringes and transfer of liquid medicaments would be advanced. Such a device is described hereinbelow.

SUMMARY

A fluid transfer device of the present invention useful for accessing fluid from vials and ampoules includes a cannula assembly that defines an axis. The cannula assembly includes a cannula with a proximal end, a distal end and a lumen therethrough. The cannula assembly also has a hub fixedly attached to the proximal end of the cannula that has an open proximal end in fluid communication with the lumen. The fluid transfer device also includes a filling straw with a proximal end, a distal end, a passageway therethrough and a housing with an outside surface that is fixedly attached to the proximal end of the straw. The housing has a cavity therein to coaxially receive at least a portion of the cannula assembly to form a fluid path between the open proximal end of the hub and the distal end of the filling straw. The fluid transfer device also has a removable shield with an open proximal end, a distal end, an outside surface, and a sidewall that defines a receptacle therein. The shield is disposed so that the filling straw and at least a portion of the housing is within the receptacle. The shield is rotatable with respect to the housing from a first position wherein the shield is removable from the housing to expose the filling straw for use and a locked position wherein the shield and the housing are locked together to form a unitary structure. The unitary structure is then removable from hub to expose the cannula. The outside surface the housing and the outside surface of the shield further comprise an indication of the shield's rotational position with respect to the housing.

When the fluid transfer device of the invention is mounted on a syringe, it allows a practitioner to selectively expose a filling straw to withdraw fluid from an ampoule or a vial with a resilient closure, then replace the shield and lock it onto the housing. Subsequent removals of the shield then expose a cannula for delivery of the dosage. In many hospital dose administration practices, the dosages are often prepared at pharmacy locations remote from the location where the dosage will be administered to the patient. Many parenterals are available in unit dose ampoules or in multi-dose vials with resilient closures that require an elongate penetrating element to access the drug. Previously, the pharmacy would simply have used a conventional hypodermic needle both for filling the syringe and delivery directly into the patient, into a catheter or a delivery reservoir. With the recognition of the hazards of blood borne pathogens, many medication delivery protocols now specify the use of a blunt cannula to introduce a parenteral medicament into a catheter or a delivery reservoir and elimination of sharp hypodermic needles. However, practitioners still often need to make a penetration of an vial septum to fill a syringe. The device of the invention allows a practitioner to fill a syringe by penetrating a septum and then provides a blunt cannula without having to remove the filling straw and replace it with a blunt cannula for administration. The fluid transfer device of the invention is simple to use and simplifies the hospital pharmacy practitioners protocols and inventory.

DETAILED DESCRIPTION

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. For the purpose of this disclosure, the term "proximal" refers to the portion of the invention closest to the practitioner and the term "distal" refers to the portion of the device closest to the patient.

Figure 5:
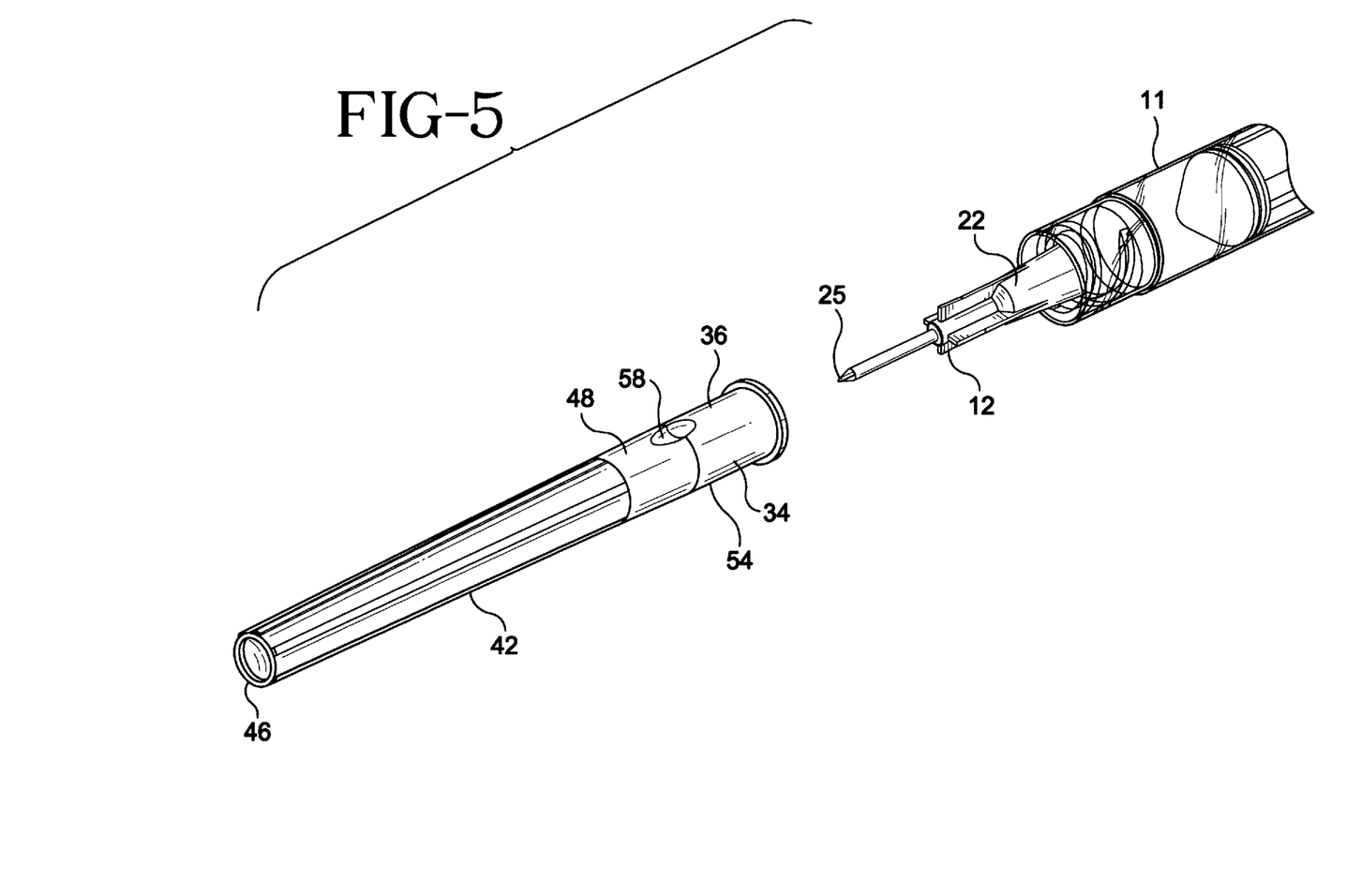
FIG. 5 is a perspective view of the device of FIG. 1 with the shield and housing removed from the hub.

Referring to FIGS. 1–7, a fluid transfer device 10 of the present invention useful for accessing fluid from vials and ampoules includes a cannula assembly 12 that defines an axis "A". Cannula assembly 12 includes a cannula 14 with a proximal end 16, a distal end 18 and a lumen 20 therethrough. Cannula assembly 12 also has a hub 22 fixedly attached to proximal end 16 of the cannula that has an open proximal end 24 in fluid communication with lumen 20. Preferably, open proximal end 24 of cannula assembly 12 is formed into a blunt rounded point 25. Fluid transfer device 10 also includes a filling straw 26 with a proximal end 28, a distal end 30 and a passageway 32 therethrough. Filling straw 26 also includes a housing 34 with an outside surface 36 that is fixedly attached to proximal end 28 of the straw. Housing 34 has a cavity 38 therein to coaxially receive at least a portion of the cannula assembly to form a fluid path 40 between open proximal end 24 of the hub and distal end 30 of the filling straw. Fluid transfer device 10 also has a removable shield 42 with an open proximal end 44, a preferably closed distal end 46, an outside surface 48, and a sidewall 50 that defines a receptacle 52 therein. Shield 42 is disposed so that filling straw 26 and at least a portion of housing 34 is within receptacle 52. Shield 42 is rotatable with respect to housing 34 from a first position, best seen in FIGS. 1 and 3, wherein shield 42 is removable from housing 34 to expose filling straw 26 for use and a locked position, best seen in FIGS. 5, 6 and 7 wherein shield 42 and housing 34 are locked together to form a unitary structure 54. As best seen in FIG. 5, unitary structure 54 is then removable from hub 22 to expose the cannula. Outside surface 36 of the housing and outside surface 46 of the shield further comprise an indication 58 of the rotational position of shield 42 with respect to housing 34. Preferably, indication 58 is an alteration in surfaces 36 and 48 as shown in the FIGS. 1–7, thus providing both a visual and tactile indication to the practitioner of the position of shield 42 with respect to housing 34. Alternatively (not shown), indication 58 could be a line, other mark or a color change.

Figure 6:
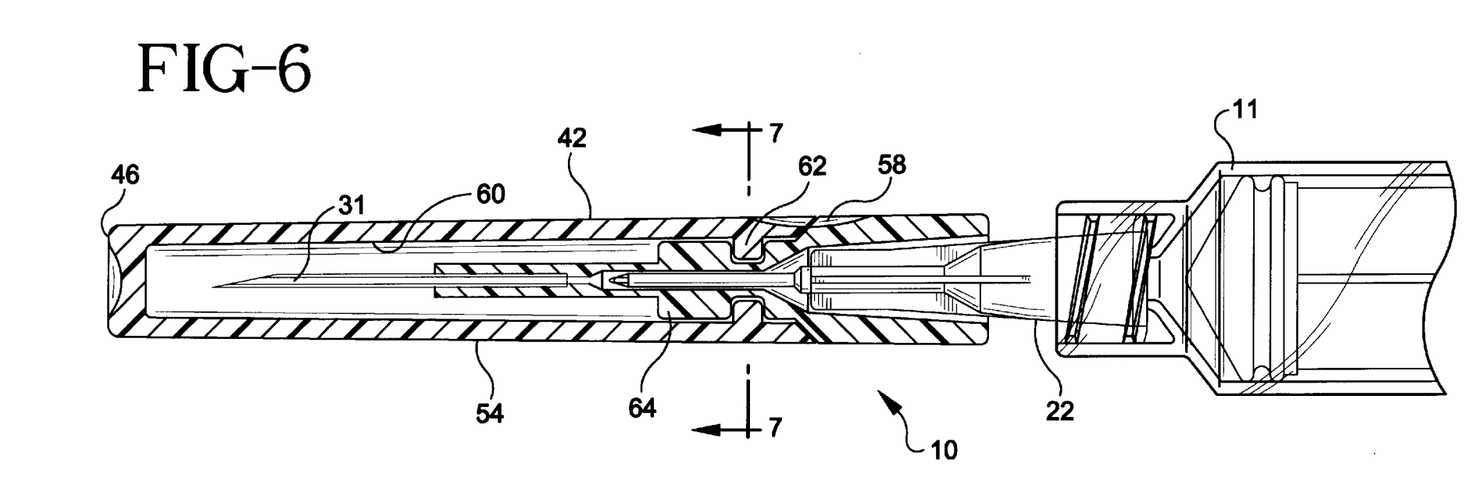
FIG. 6 is a longitudinal cross-sectional of the device of FIG. 1, mounted on a fluid handling device with the shield in the locked position relative to the housing.
Figure 7:
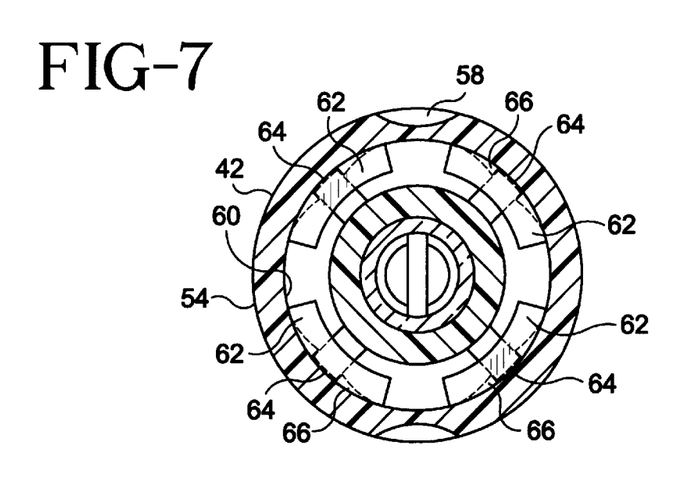
FIG. 7 is a cross-sectional view of the device of FIG. 1 taken along the line 6—6 with the shield in the locked position relative to the housing.
Figure 8:
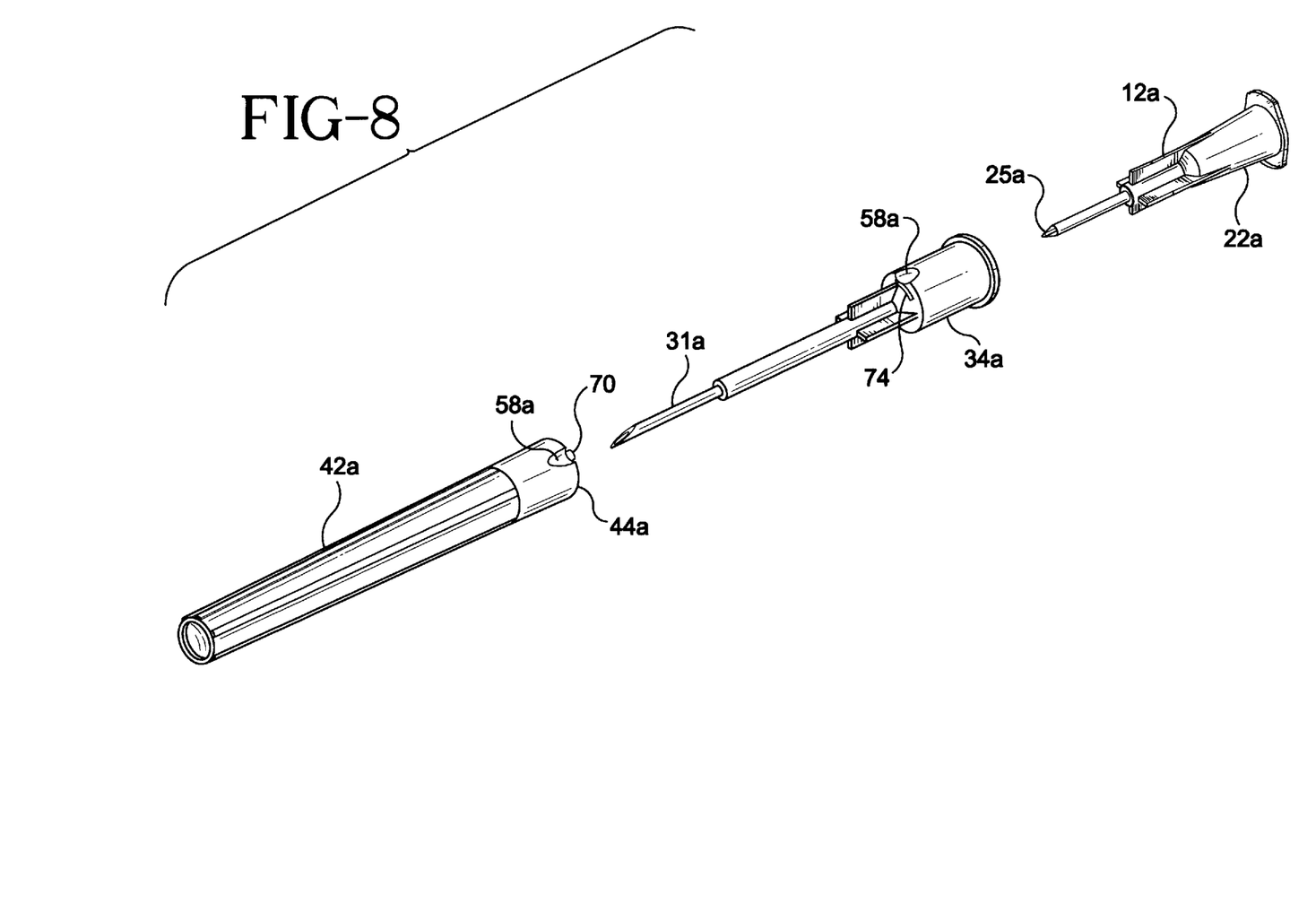
FIG. 8 is an exploded perspective view of an alternate embodiment of the fluid transfer device of the invention.
Figure 9:
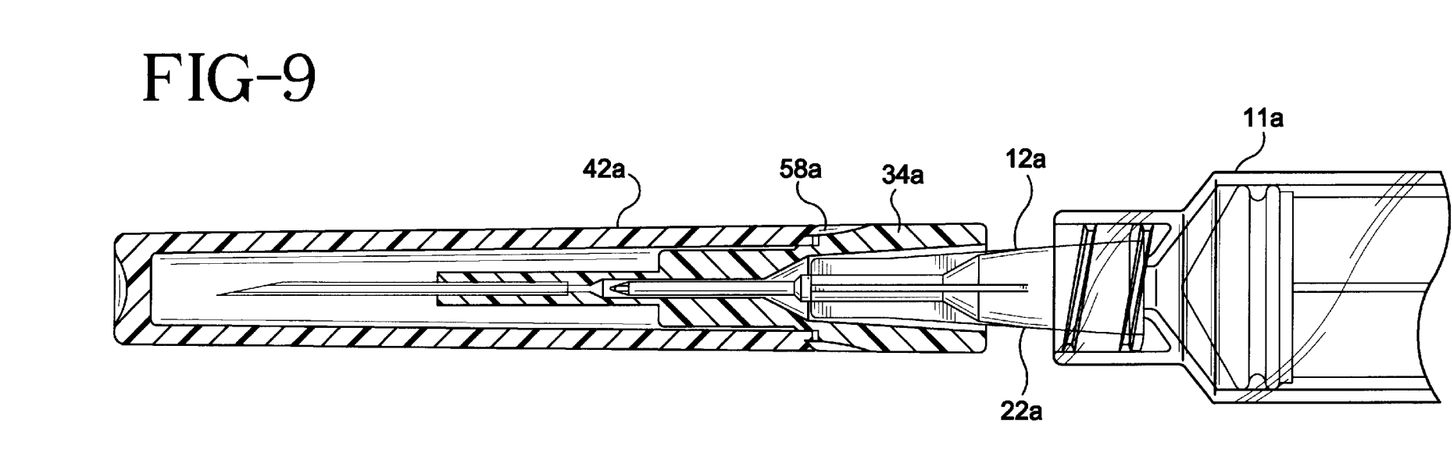
FIG. 9 is a longitudinal cross-section of the invention of FIG. 8, analogous to FIG. 3, with the shield in the first position relative to the housing.
Figure 10:
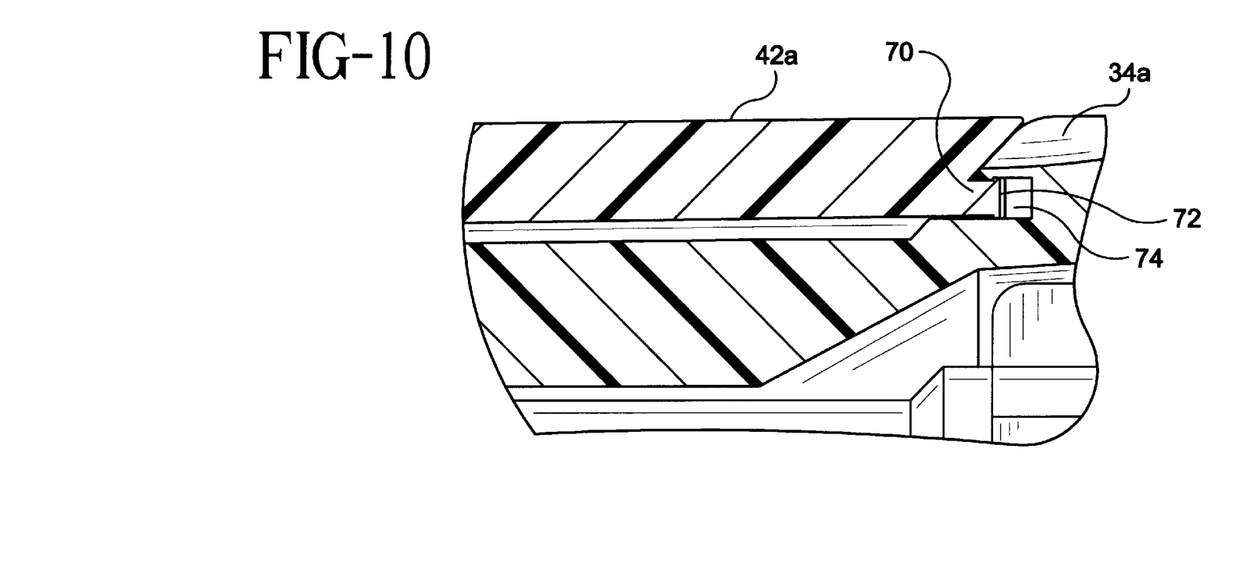
FIG. 10 is an enlarged cross-sectional detail, taken from FIG. 9, of the invention of FIG. 8 with the shield in the first position relative to the housing.
Figure 11:
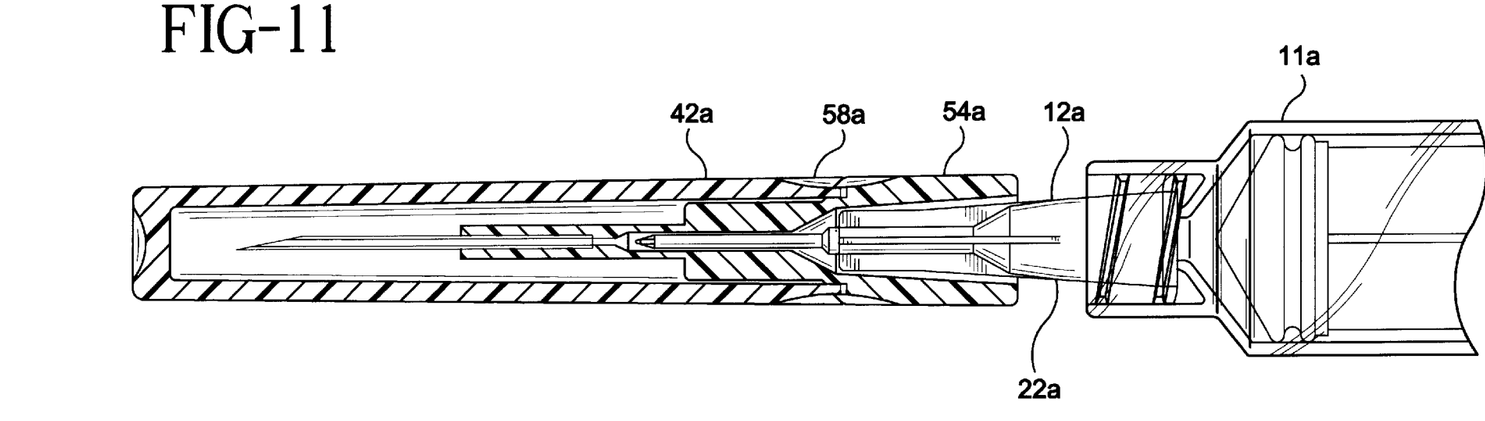
FIG. 11 is a longitudinal cross sectional view, analogous to FIG. 9, with the shield in the locked position relative to the housing.
Figure 12:
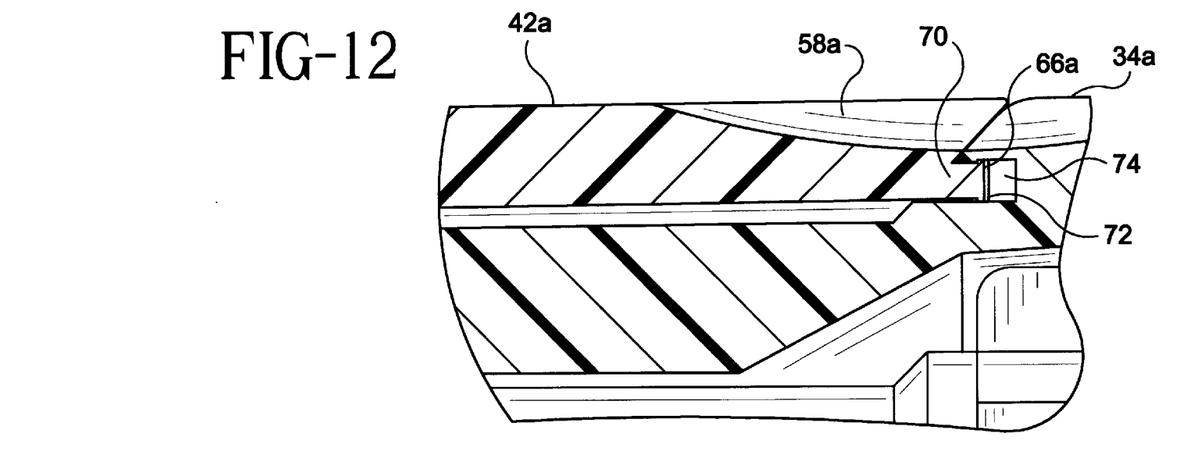
FIG. 12 is an enlarged cross-sectional detail, taken from FIG. 11 with the shield in the locked position relative to the housing.

Referring to FIGS. 6 and 7, shield 42 has an interior surface 60, that preferably has at least one shoulder 62 disposed to interact with at least one lug 64 on the portion of housing 34 that is within shield 42 when filling straw 26 is disposed within the shield. Lug 64 and shoulder 62 are disposed to substantially irreversibly engage with a latch 66 when shield 42 is rotated from first position to locked position. Preferably, as shown in FIG. 7, there are four shoulders 62 on the shield and four lugs 64 on the housing to ensure that unitary structure 54 is well engaged. When latch 66 is engaged, a distal force for removing unitary structure 54 from hub 22 is less than a force for moving shield 42 from the locked position to the first position thereby substantially preventing inadvertent access to filling straw 26 after shield 42 is rotated from the first position to the locked position.

Figure 2:
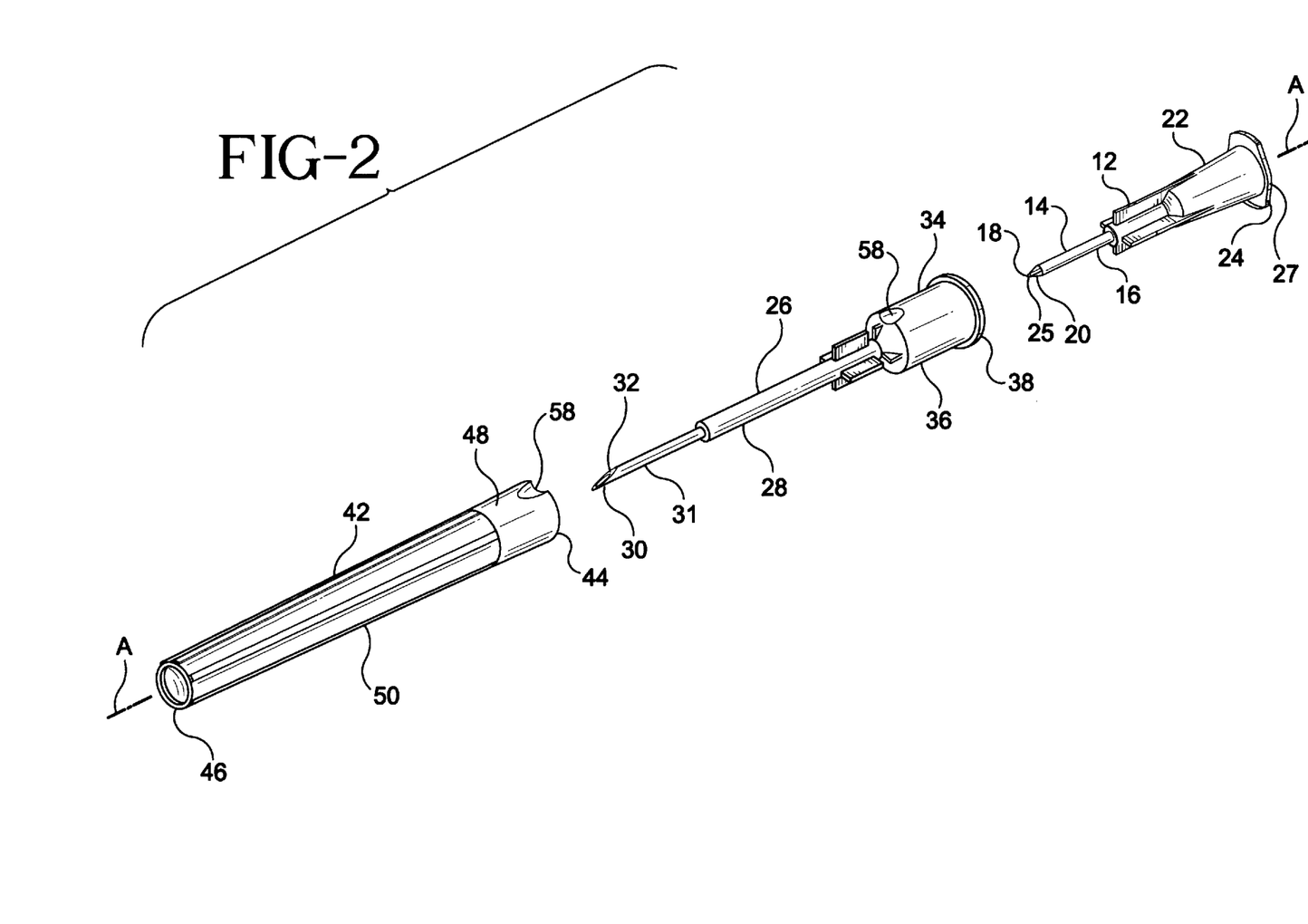
FIG. 2 is an exploded perspective view of the fluid transfer device of FIG. 1.
Figure 3:
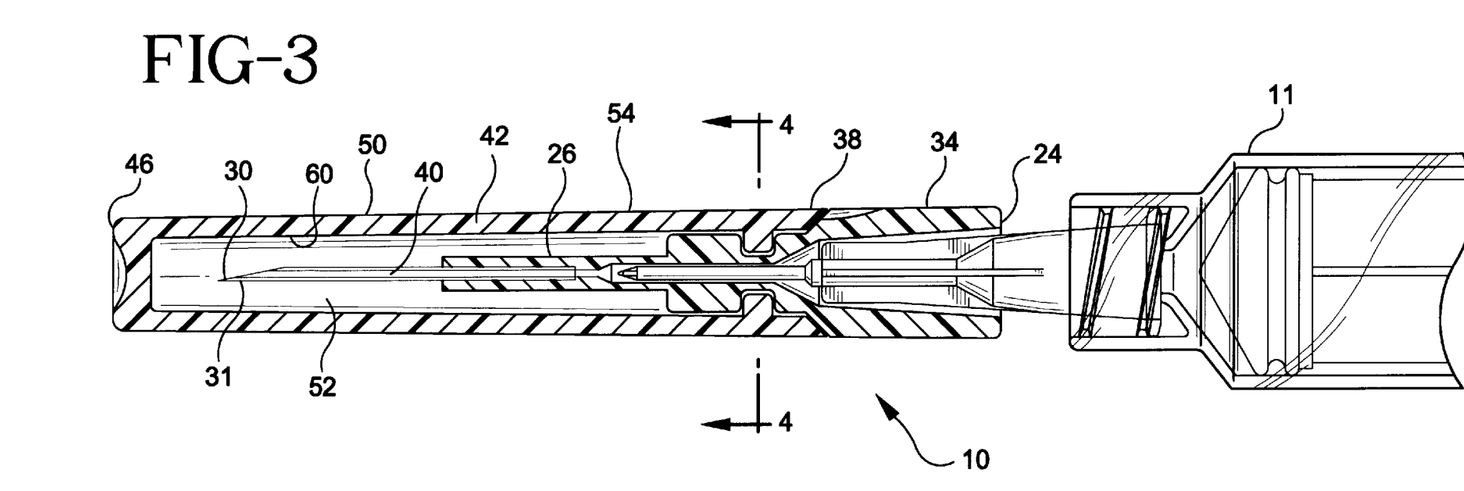
FIG. 3 is a longitudinal cross-sectional view of the device of FIG. 1, mounted on a fluid handling device with the shield in the first position relative to the housing.
Figure 4:
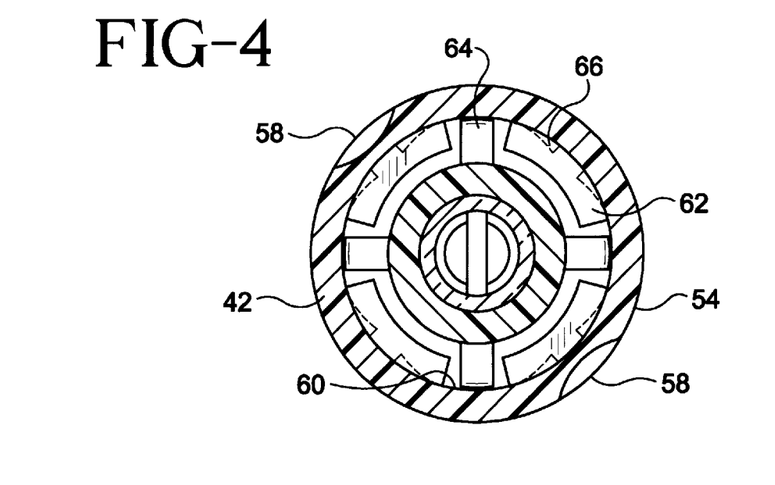
FIG. 4 is a cross-sectional view of the device of FIG. 1, taken along the line 4—4 with the shield in the first position relative to the housing.

Referring to FIG. 2, filling straw 26 has a distal portion 31 that may be formed from stainless steel. Alternatively, distal portion 31 may be integrally formed as a single article of manufacture with housing 34 from a thermoplastic material such as polyethylene, polypropylene, polycarbonate, acrylonitrile/butadiene/styrene (ABS), polyamide, polyacetal, copolymers of these thermoplastic materials and the like. Preferably distal point of the filling straw is formed with a sharpened surface that describes a beveled surface with axis A to facilitate penetration of the filling straw through resilient stoppers of parenteral vials.

Preferably, as shown in the figures, hub 22 of the cannula assembly has a female luer fitting 27 at open proximal end 24 to facilitate attachment of fluid transfer device 10 to a syringe 11 or other fluid handling devices that have male luer fittings. Cannula assembly 12 is preferably formed as a single article of manufacture from a thermoplastic material such as polyethylene, polypropylene, polycarbonate, acrylonitrile/butadiene/styrene (ABS), polyamide, polyacetal, copolymers of these thermoplastic materials and the like.

Figure 1:
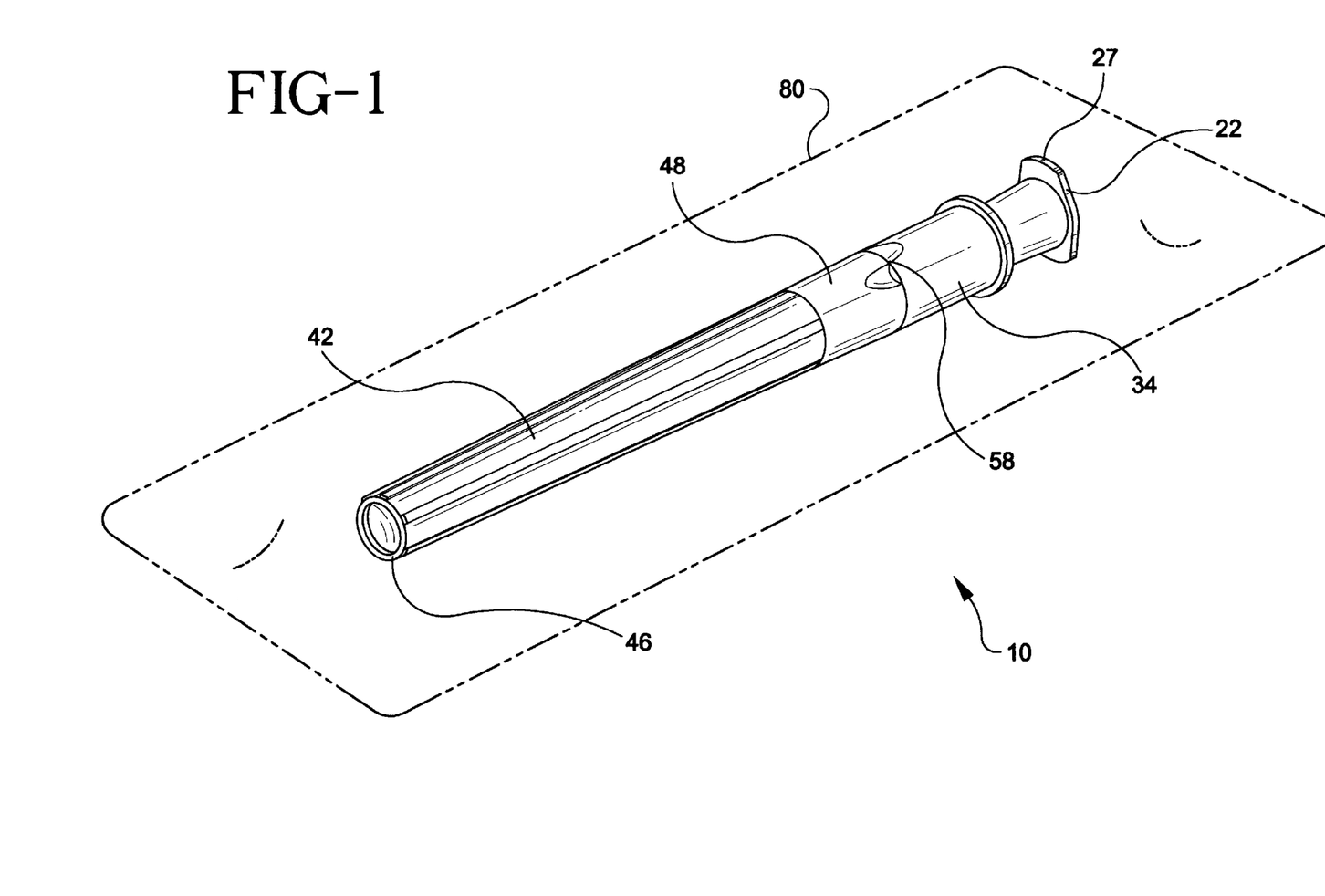
FIG. 1 is a perspective view of the fluid transfer device of the invention.

As shown in phantom in FIG. 1, fluid transfer device 10 preferably is sealed in a package 80 that is formed from materials substantially resistant to the passage of microorganism and exposed to conditions that render any microorganisms inside package 80 substantially non-viable. Suitable materials for forming package 80 include, but are not limited to paper, polymeric film, composites of paper and polymeric films, spun-bonded non-wovens and combinations of these materials. Suitable conditions for rendering microorganisms substantially non-viable include, but are not limited to, chemical sterilant agents such as ethylene oxide, gaseous hydrogen peroxide and the like as well as ionizing radiation such as is produced by $CO^{60}$, electron beam and the like. Consideration of the sterilization method should be made when selection of materials for forming device 10 and package 80 are made to ensure that the materials selected compatible with the sterilization conditions. When subjected to a validated sterilization in package 80, device 10 may be considered sterile as long as the package is intact.

A preferred method for filling a fluid handling device such as syringe 11 from a liquid medicament vial with a resilient closure with device 10 includes removing shield 42 to expose filling straw 26. Filling straw 26 with preferred sharp distal point 30 is then used to penetrate the resilient vial closure and allow the practitioner to withdraw the desired volume of liquid medicament into the syringe. The practitioner then replaces shield 42 onto housing 34 to cover the used filling straw and observes indication 58. The practitioner then rotates shield 42 with respect to housing 34 from the first position to the second position, thereby engaging latch 66 and rendering shield 42 and housing into unitary structure 54. Engagement of latch 66 substantially prevents inadvertent access to filling straw 26 with sharp distal point 30. When the fluid handling device with the liquid medicament therein is delivered to the administration location, the practitioner then removes the now unitary structure 54 to expose the cannula assembly 12 to administer the medicament to the patient. When cannula 12 includes preferred blunt rounded point 25, the cannula is generally used with a pre-slit septum.

Referring to FIGS. 8–12, an alternate embodiment to the fluid transfer device of FIGS. 1–7 is illustrated. In this embodiment, there are elements similar in structure and function to the embodiment of the present invention shown in FIGS. 1–7. Accordingly, substantially similar components that perform substantially similar functions are numbered identically to those components of the embodiment of FIGS. 1–7 except that a suffix a is added to identify those components in FIGS. 8–12. In this embodiment, shield 42a includes a tab 70 projecting proximal therefrom having a proximal flange 72 and housing 34a includes a distal slot 74 for receiving tab 70 when shield 42a is disposed on the portion of housing 34a. Slot 74 is sized and shaped to substantially irreversibly engage tab proximal flange 72 forming a latch 66a when shield 42a is rotated from the first position to the locked position. When latch 66a is engaged, a distal force for removing unitary structure 54a from hub 22a is less than a force for moving shield 42a from the locked position to the first position thereby substantially preventing inadvertent access to filling straw 26a after shield 42a is rotated from the first position to the locked position.

When fluid transfer device 10 is used with a syringe, the device allows a practitioner to selectively expose a filling straw to withdraw fluid from an ampoule or a vial with a resilient closure, then replace the shield and lock it onto the housing. Subsequent removals of the shield only expose the cannula assembly for delivery of the dosage. As was described above, in many hospital dosage administration protocols, the dosages are often prepared at locations, such as a pharmacy, that are remote from the location where the dosage is actually administered to the patient. Many parenterals are available in unit dose ampoules or in multi-dose vials with resilient closures that require an elongate penetrating element to access the drug. Previously, the pharmacy would simply have used a conventional hypodermic needle both for filling the syringe and delivery directly into the patient, into a catheter or a delivery reservoir. With the recognition of the hazards of blood borne pathogens, many medication delivery protocols now specify elimination of sharp hypodermic needles and the use of a blunt cannula to introduce a parenteral medicament into a catheter or a delivery reservoir. However, practitioners still often need to make a penetration of a vial septum to fill a syringe. The device of the invention allows a practitioner to fill a syringe with a penetrating element and then provides a blunt cannula for the ultimate delivery without requiring the practitioner to remove the filling straw and replace it with a blunt cannula for administration. The fluid transfer device of the invention is simple to use and simplifies the hospital pharmacy practitioners' protocols and inventory.

What is claimed is:

1. A fluid transfer device for accessing fluid from vials and ampoules comprising:

a cannula assembly defining an axis and including a cannula having a proximal end, a distal end and a lumen therethrough, a hub fixedly attached to said proximal end of said cannula having an open proximal in fluid communication with said lumen;

a filling straw having a proximal end, a distal end and a passageway therethrough, a housing with an outside surface fixedly attached to said proximal end of said straw, said housing having a cavity therein to coaxially receive at least a portion of said cannula assembly to form a fluid path between said open proximal end of said hub and said distal end of said filling straw;

a removable shield having an open proximal end, a distal end and a sidewall having an outside surface and defining a receptacle therein, said shield being disposed so that said filling straw and at least a portion of said housing is within said receptacle, said shield being rotatable with respect to said housing from a first position wherein said shield is removable from said housing to expose said filling straw for use, and a locked position wherein said shield and said housing are locked together to form a unitary structure, said unitary structure being removable from said hub to expose said cannula; and wherein said outside surface and of said housing and said outside surface of said shield further comprise an indication of said shield rotational position with respect to said housing.

2. The fluid transfer device of claim 1 wherein a force for removing said unitary structure from said hub is less than a force for moving said shield from said locked position to said first position thereby substantially preventing inadvertent access to said filling straw after said shield is rotated from said first position to said locked position.

3. The fluid transfer device of claim 1 wherein said outside surface of said housing includes an indicator and said outside surface of said shield includes an indicator, said indicators being non-aligned when said shield is in said first position with respect to said housing and said indicators being substantially aligned when said shield is in said locked position with respect to said hub.

4. The fluid transfer device of claim 3 wherein said indicator on said shield and said indicator on said housing each comprises an alteration in each of said outside surfaces, said alteration in said surfaces being sufficient to be visually and tactilely perceptible to a practitioner, said shield being removable to expose said filling straw when said surface alterations are not in alignment and wherein said shield and said housing are removable together as said unitary structure to expose said cannula when said surface alterations are substantially aligned.

5. The fluid transfer device of claim 4 wherein said shield includes an interior surface, said interior surface including at least one shoulder and said housing includes at least one lug on said portion of said housing within said shield when said filling straw is disposed within said shield, said lug and said shoulder being disposed to substantially irreversibly engage when said shield is rotated from said first position to said locked position.

6. The fluid transfer device of claim 4 wherein said shield includes a tab projecting proximally therefrom having a proximal flange and said housing includes a distal slot for receiving said tab when said shield is disposed on said portion of said housing, said slot being sized and shaped to substantially irreversibly engage said tab proximal flange when said shield is rotated from said first position to said locked position.

7. The fluid transfer device of claim 1 wherein said distal end of said shield is closed.

8. The fluid transfer device of claim 1 wherein said distal end of said cannula comprises a blunt rounded point.

9. The fluid transfer device of claim 1 wherein said distal end of said hub further comprises a female luer fitting.

10. The fluid transfer device of claim 1 wherein said distal end of said filling straw further comprises a sharpened surface that describes a bevel with said axis.

11. The fluid transfer device of claim 1 wherein said filling straw further comprises a distal portion with said housing being formed from a thermoplastic material.

12. The fluid transfer device of claim 11 wherein said filling straw further comprises a distal portion with said housing forming a bevel with said axis.

13. The fluid transfer device of claim 12 wherein said filling straw distal portion is formed from stainless steel.

14. The fluid transfer device of claim 12 wherein said filling straw distal portion and said housing are formed as a single article of manufacture from a thermoplastic material.

15. The fluid transfer device of claim 14 wherein said thermoplastic material is selected from the group consisting of polyethylene, polypropylene, polycarbonate, acrylonitrile/butadiene/styrene (ABS), polyamide, polyacetal and copolymers thereof.

16. The fluid transfer device of claim 1 wherein said device is sealed in a package formed from materials resistant to the passage of microorganisms and exposed to conditions rendering any microorganisms in said package non-viable.

17. A fluid transfer device for accessing fluid from vials and ampoules comprising:

a cannula assembly defining an axis and including a cannula having a proximal end, a distal end and a lumen therethrough, a hub fixedly attached to said proximal end of said cannula having an open proximal in fluid communication with said lumen;

a filling straw having a proximal end, a distal end and a passageway therethrough, a housing with an outside surface fixedly attached to said proximal end of said straw, said housing having a cavity therein to coaxially receive at least a portion of said cannula assembly to form a fluid path between said open proximal end of said hub and said distal end of said filling straw;

a removable shield having an open proximal end, a distal end, an outside surface, and a sidewall defining a receptacle therein, said shield being disposed so that said filling straw and at least a portion of said housing is within said receptacle, said shield being rotatable with respect to said housing from a first position wherein said shield is removable from said housing to expose said filling straw for use and a locked position wherein said shield and said housing are locked together to form a unitary structure, said unitary structure being removable from said hub to expose said cannula, and wherein a force for removing said unitary structure from said hub is less than a force for moving said shield from said locked position to said first position thereby substantially preventing inadvertent access to said filling straw after said shield is moved from said first position to said locked position; and wherein said outside surface of said housing includes an indicator and said outside surface of said shield each include an indicator, said indicators being non-aligned when said shield is in said first position with respect to said housing and said indicators being substantially aligned when said shield is in said locked position with respect to said hub.

* * * * *